United States Patent [19]
Jacobson et al.

[11] Patent Number: 5,462,060
[45] Date of Patent: Oct. 31, 1995

[54] METHODS AND APPARATUS FOR DETERMINING WHEN TACHYARRYTHMIA IS PACE-TERMINABLE

[75] Inventors: Peter Jacobson, Haguenau; Daniel Kroiss, Schweighouse-Moder; Christine Henry, Paris, all of France

[73] Assignee: ELA Medical, S.A., Montrouge, France

[21] Appl. No.: 248,329

[22] Filed: May 24, 1994

[30] Foreign Application Priority Data

May 28, 1993 [FR] France .................. 93 06406

[51] Int. Cl.$^6$ ............................. A61B 5/0464
[52] U.S. Cl. ..................................... 128/702
[58] Field of Search ...................... 128/702, 705

[56] References Cited

U.S. PATENT DOCUMENTS

| | | |
|---|---|---|
| 3,554,187 | 1/1971 | Glassner . |
| 3,606,882 | 9/1971 | Abe et al. . |
| 3,946,725 | 3/1976 | Bolshov et al. . |
| 4,181,135 | 1/1980 | Andresen et al. ............ 128/703 |
| 4,860,749 | 8/1989 | Lehmann . |
| 5,042,497 | 8/1991 | Shapland . |
| 5,054,485 | 10/1991 | Cohen . |
| 5,107,850 | 4/1992 | Olive .......................... 128/705 |
| 5,205,283 | 5/1993 | Olson . |

FOREIGN PATENT DOCUMENTS

| | | | |
|---|---|---|---|
| 0360412 | 3/1990 | European Pat. Off. ....... A61N 1/365 |
| 0395242 | 10/1990 | European Pat. Off. ....... A61N 1/39 |
| 0401962 | 12/1990 | European Pat. Off. ....... A61N 1/368 |
| 0436517 | 10/1991 | European Pat. Off. ....... A61N 1/368 |
| 0540141 | 5/1993 | European Pat. Off. ....... A61N 1/368 |
| WO93/02746 | 2/1993 | WIPO ........................ A61N 1/368 |

OTHER PUBLICATIONS

R. A. Default et al., Computers In Cardiology, "Dual Lead Fibrillation Detection for Implantable Defibrillators Via LMS Algorithm", Oct. 7, 1986, Boston US, pp. 164–166.

K. B. Otte et al., "Physiologische Elektrostimulation des Herzens Stand und Entwicklungsaussichten" Medizintechnik, Sep. 1984, pp. 84–91.

*Primary Examiner*—William E. Kamm
*Assistant Examiner*—Scott M. Getzow
*Attorney, Agent, or Firm*—Davis Hoxie Faithfull & Hapgood

[57] ABSTRACT

Methods and apparatus for classifying cardiac rhythm by analyzing sensed atrial and ventricular heartbeats, and determining if the rhythm might be pace-terminable in a given chamber. The method maintains a histogram of the sensed beat interval in the chamber of interest and a second histogram of conduction time from the other chamber. The method classifies a rhythm as pace terminable in the given chamber when the intervals in that chamber are stable, and the conduction times to that chamber are unstable. It applies further criteria when the intervals in the given chamber are stable, and the conduction times are also stable. Antitachycardia pacing is deliverable to terminate tachyarrhythmias determined to be pace terminable.

81 Claims, 1 Drawing Sheet

METHODS AND APPARATUS FOR DETERMINING WHEN TACHYARRYTHMIA IS PACE-TERMINABLE

FIELD OF THE INVENTION

This invention relates to medical devices which monitor the cardiac state of a patient by sensing-atrial and ventricular heartbeats, and which analyze these signals to determine if a tachyarrhythmia is present, and, when present, to determine if the tachyarrhythmia is of a type which might be reverted by antitachycardia pacing.

BACKGROUND OF THE INVENTION

As used herein, the term "pacing" refers to the delivery of a stimulation pulse to cardiac tissue, the term "antitachycardia pacing" (or ATP) refers to the delivery of any of one or more stimulation pulses that are intended to revert a tachyarrhythmia, including ventricular and/or atrial pacing, and the term "tachyarrhythmia" refers to a rapid abnormal cardiac rhythm, including ventricular fibrillation (VF), ventricular tachycardia (VT), sinus tachycardia (ST), and superventricular tachycardia (SVT); SVT includes atrial tachycardia, atrial flutter, and atrial fibrillation; a normal cardiac rhythm without tachyarrhythmia is called sinus rhythm (SR).

The medical devices that are the subject of this invention sense atrial and ventricular cardiacsevents (or beats), and derive therefrom one or more of the following intervals: between ventricular beats (RR), between atrial beats (PP), from an atrial beat to a ventricular beat (PR), and from a ventricular beat to an atrial beat (RP). They alternatively or in addition count the number of atrial beats (events) (Na) or ventricular beats (events) (Nv) in a predetermined number of cardiac cycles. As used herein, the term beat is synonymous with cardiac events, depolarization, complexes, and a heartbeat.

Arzbaecher, Bump, Jenkins, et al. PACE, Vol. 7, pp. 541–547 (1984) recognized that sensing heartbeats in a single chamber to determine when to apply ATP in that chamber, may result in inappropriate pacing and subsequent acceleration or even initiation of a tachycardia. They proposed sensing both atrial and ventricular heartbeats, and dividing intermediate-rate tachyarrhythmias into three zones: (1) When Nv>>Na, they classified this as VT; (2) When Na>>Nv, they classified this as SVT or ST; and (3) When Na approximately equals Nv, they applied one of two VT criteria: (a) acceleration of ventricular rate exceeding a preset limit, and (b) change in ventricular rate, following a premature atrial stimulus, not exceeding a preset limit.

Schuger, Jackson, Steinman and Lehmann, PACE, Vol. 11, pp. 1456–1464 (1988), proposed a criterion for distinguishing VT, consisting of stable RR and unstable PR. They further suggested averaging these PR and RR measurements over several cycle lengths to avoid falsely satisfying the VT criterion on premature ventricular contractions (PVCs).

U.S. Pat. No. 4,860,749 to Lehmann divided intermediate-rate ventricular rhythms into three zones: RR<PP (equivalent to Arzbaecher's Nv>>Na), RR=PP (equivalent to Nv=Na) and RR>PP (equivalent to Nv<<Na). Lehmann classified RR<PP as VT. For RR>PP, Lehmann applied the VT criterion: RR stable and PR unstable. For RR=PP, Lehmann applied the VT criterion: PR longer than PR in sinus rhythm.

The inventors have recognized that .the background art proposes a stability criterion for determination of pace-terminable ventricular tachyarrhythmias, where it detects pace-terminable VT when there is RR stability and PR instability. This method has as its origin the expectation that in pace-terminable VT, most ventricular beats are caused by a preceding ventricular beat, conducted by a circular pathway with stable conduction time. However, when most ventricular beats are caused by atrial beats, conducted by an atrioventricular pathway with stable conduction time, then this is not pace-terminable VT.

The background art recognizes that this criterion applies when there is not 1:1 atrioventricular association. However, when there is 1:1 association, the criterion cannot always distinguish an atrial tachyarrhythmia conducted to the ventricle from a ventricular tachyarrhythmia conducted to the atrium.

Hence, the inventors also have realized that there are deficiencies in the background art, particularly in the calculation and application of the stability criterion. In this regard, the Lehmann U.S. Pat. No. 4,860,749 does not disclose which atrial beat or beats to take into account when calculating the PR interval. When Na>Nv, more than one atrial beat can be detected per ventricular cycle. If more than one PR interval per cycle is taken into account in an averaging calculation of stability, this will make the PR interval appear unstable, even though atrioventricular conduction with fixed block and very stable PR interval may be in progress.

In addition, the aforementioned background art only applies the stability criterion when Na>Nv. As recognized by the inventors, if one considers the onset of ST with Na=Nv, the RR interval decreases (the rate accelerates), but PR remains constant. Thus, as the inventors have appreciated as discussed below, the stability criterion could be applied to classify this, correctly, as not VT.

The Lehmann U.S. Pat. No. 4,860,749 does not disclose how to calculate PR instability or RR stability. The Schuger publication (with Lehmann) does suggest to use averages over several cardiac cycles. However, this technique is grossly affected by a single premature beat, a burst of electrical noise, or by a single heartbeat which is not sensed.

The inventors also have recognized that the stability criterion could be applied to detecting pace-terminable tachyarrhythmias in the atrium as well as the ventricle.

OBJECTS AND SUMMARY OF THE INVENTION

It is, therefore, an object of the invention to improve the specificity for detection of pace-terminable tachyarrhythmias, particularly for tachyarrhythmias in an intermediate rate range. It is another object to improve the specificity by sensing atrial and ventricular heartbeats and processing the cardiac events detected over time with respect to the cardiac chamber suspected of originating the tachycardia.

The present invention provides improved specificity of pace-terminable tachyarrhythmia detection in a first chamber by providing a criterion requiring stability in that first chamber, and conduction instability from the second chamber. The invention also pertains to determining when a tachyarrhythmia is pace-terminable in the atrium or in the ventricle. Broadly the present invention concerns apparatus and methods for sensing atrial and ventricular cardiac activity, taking into account all sensed beats from the second chamber which could have been conducted to a sensed beat in the first chamber, in addition to the beat in the first chamber immediately preceding the beat in the first chamber, applying the criterion to all rhythms in the first chamber, including rhythms with 1:1 association, to declare that rhythms without stability in that chamber are not pace-terminable, and calculating stability in such a manner that a few premature beats, incidence of electrical noise, or unsensed heartbeats in either chamber do not grossly affect the calculation. The foregoing analysis is applied to either or both chambers.

More particularly, the present invention relates to medical devices which, when applied in the ventricle, first identify VF as occurring with a ventricular rate above some first preset rate, and SR as occurring with a ventricular rate below some second preset rate; and then attempt to classify the remaining rhythms with rates between these two rates. Thus, the invention also applies to devices which attempt to distinguish VT from ST or SVT in some intermediate range of rates.

The invention also concerns devices which deliver therapy after analyzing the cardiac rhythm and those that do not. It also applies to implantable and/or external devices. And it applies to the analysis of rhythms before, during, and after therapy. As used herein, the term "therapy" includes ATP, cardioversion, and defibrillation which are known and provided in a conventional manner.

Where these devices involve comparing measured or determined quantities to preset or predetermined limits, fractions, or values, the limits, fractions, or values, may be fixed or they may be programmable.

According to one particular aspect of the invention, the apparatus and methods concern the creation and maintenance of a histogram of recent intervals in the first chamber, and a histogram of recent conduction intervals from the second chamber to the first chamber during the same cardiac cycle, sorted in bins according to their lengths, obtaining an auto-correlation total, and a cross-correlation total, i.e., the total number of counts of events recorded in the respective histograms. The histograms are then used to evaluate the following criteria (1) auto-correlation peak, i.e., the maximum number of recent intervals in the first chamber which meet a preset stability criterion; and (2) Cross-correlation peak, i.e, the maximum number of conduction intervals from the second chamber which meet a preset conduction time (stability) criterion.

In accordance with an embodiment of the invention, stability in the first chamber is declared when the auto-correlation peak, divided by the auto-correlation total, exceeds a preset fraction, and conduction stability is declared when the cross-correlation peak, divided by either the auto-correlation peak (in a first embodiment of the invention) or by the auto-correlation total (in a second embodiment), exceeds a preset fraction. The first embodiment of the invention compares the relative stability of conduction between chambers and conduction from the same chamber. The second variant compares the stability of each to preset limits.

When there is no stability in the first chamber, the tachyarrhythmia probably is not pace-terminable in the first chamber. Hence, the tachyarrhythmia is declared not pace-terminable in that chamber.

When there is stability in the first chamber, but not conduction stability, this means that the tachyarrhythmia probably has its origin in the first chamber, and it is declared pace-terminable in that chamber.

When there is stability in the first chamber, and conduction stability, it must then be determined whether the conduction is 1:1 or many:1 from the second chamber. When the cross-correlation peak, divided by the cross-correlation total, exceeds a preset fraction, a 1:1 association ratio is declared. On the other hand, when the total number of events counted in the second chamber (Cross-correlation total) divided by the total number of events counted in the first chamber (auto-correlation total) results in a number near 1, for example, in a range of from 0.66 to 1.33, a 1:1 association ratio is declared and otherwise a many:1 association ratio is declared.

In the case of a declared 1:1 association ratio, another criterion is then used, for example, the presence of rate acceleration originating with disassociation at the onset of acceleration, to determine if the tachyarrhythmia is pace-terminable. In the case of a declared many:1 association ratio, the invention concludes that the tachyarrhythmia is not pace-terminable in the first chamber, since it originates in the second chamber.

In another aspect, the present invention provides apparatus and methods for analyzing cardiac activity by sensing atrial and ventricular signals corresponding to cardiac activity to determine if a tachyarrhythmia is pace-terminable, characterized by determining the auto-correlation peak, based on recent intervals between cardiac signals detected in a first chamber satisfying a stability criterion, and determining the cross-correlation peak, based on recent cardiac signals detected in the same first chamber that correspond to signals detected in a second chamber, and are detected within a predetermined conduction time limit. It should be understood that the cross-correlation histogram may contain a plurality of intervals corresponding to a single beat in the first chamber, and although only one of those intervals can result from conduction, all of them are considered "conduction intervals."

The auto-correlation peak is preferably determined by maintaining a histogram of recent intervals detected in the first chamber such that the intervals are sorted by lengths into different bins, maintaining a count of the total number of events in the auto-correlation histogram, and sweeping the histogram with a predetermined window of stability to determine the maximum number of counts in the window for all possible positions of the window in the histogram. The cross-correlation peak is preferably determined by maintaining a histogram of recent conduction intervals of detected events in the second chamber being conducted to and detected in the first chamber, corresponding to the same events recorded in the auto-correlation histogram, such that the conduction intervals are sorted by lengths into different bins, maintaining a count of the total number of events in the cross-correlation histogram, and sweeping the cross-correlation histogram with a window of a predetermined conduction time limit to determine the maximum number of counts in the window for all possible positions of the window in the cross-correlation histogram.

The step of maintaining the so called histograms of recent intervals and conduction intervals preferably maintains a sliding histogram of a predetermined number of the most recent cycles, wherein a cycle is based on the occurrence of a sensed beat in the first chamber. Hence, the information corresponding to an interval occurring more than the predetermined number of cycles previously is subtracted from the histogram and the information corresponding to the most recent cycle is added to the histogram. The number of predetermined cycles may be programmable, and preferably is selected to be approximately 16.

Regarding the auto-correlation histogram, the recent intervals in the first chamber are sorted preferably in bins according to their length. As used herein, a given bin has a value that corresponds to or is the number of intervals sensed that have a length that falls within the range of time lengths associated with the bin. Similarly, in the cross-correlation histogram the recent conduction intervals from the second chamber to the first chamber are sorted in bins according to their lengths.

The sliding windows used for examining the contents of the histograms are preferably a number of contiguous bins corresponding to an interval variation, which interval variation may be programmable and is preferably approximately 64 ms. The width of such a bin is typically approximately 16 ms. In a suitable embodiment, the auto-correlation histogram records intervals having a length of between 125 ms and 600 ms, and the cross-correlation histogram records conduction intervals of between 16 ms and 500 ms.

In accordance with the invention, the foregoing analysis is preferably not undertaken for intervals of the first chamber that are longer than a predetermined limit corresponding to sinus rhythm activity, which may be programmable, and which is preferably a limit of approximately 600 ms. Stated otherwise, only fast rhythms, i.e., cardiac cycles in the first chamber above the sinus rhythm, are used in forming the histograms. In addition, in the event that no event corresponding to a fast rhythm detected in the first chamber is recorded (or registered) in the histogram for a predetermined number of cardiac cycles, for example, 16 cycles, then the histograms are reset, i.e., cleared of data, and the bin counts all returned to zero. Typically, the histograms may not be used to analyze cardiac rhythms again until after the determined intervals and conduction intervals are recorded for a preset number of fast cardiac cycles. This preset number of cardiac cycles may be programmable, and is preferably 8 (optionally one half of the number of fast cycles recorded in the histogram).

Another aspect of the present invention provides for sorting the cardiac rhythm as a function of the auto-correlation peak and auto-correlation total according to the following:

determining that there is stability in the first chamber when the auto-correlation peak, divided by the total count of events in the auto-correlation histogram, exceeds a predetermined fraction corresponding to stability; and determining that the tachyarrhythmia is not susceptible to be terminated by a stimulation pulse in the first chamber (i.e. not pace-terminable) in the absence of stability.

Another aspect of the present invention provides for sorting the cardiac rhythm as a function of the auto-correlation peak and the cross-correlation peak, characterized by:

determining a conduction instability when the cross-correlation peak divided by the auto-correlation peak does not exceed a predetermined fraction corresponding to conduction; and determining that the tachyarrhythmia is susceptible to be terminated by a stimulation pulse in the first chamber when there is stability in the first chamber and conduction instability.

Another aspect of the present invention provides for sorting the cardiac rhythm as a function of the relative values of the auto-correlation total and the cross-correlation peak, characterized by:

defining a conduction instability when the cross-correlation peak divided by the auto-correlation total does not exceed a predetermined fraction corresponding to conduction; and defining that the tachyarrhythmia is susceptible to be terminated by a stimulation pulse in the first chamber when there is stability in the first chamber and conduction instability.

Another aspect of the invention concerns the step of further sorting the cardiac rhythm having a determined stability in the first chamber and a determined conduction stability, by determining if there is a 1:1 association ratio (conduction) when the cross-correlation peak divided by the total of cross-correlation exceeds a predetermined fraction.

Another aspect of the invention concerns the step of further sorting the cardiac rhythm having a determined stability in the first chamber by determining if there is a many:1 association ratio (conduction) when the total count of events in the second chamber divided by the total of auto-correlation events exceeds a predetermined fraction.

The aforementioned predetermined fractions may be programmable.

In another embodiment of the invention, the process of sorting cardiac rhythm, i.e., determining whether a tachyarrhythmia falls into a "fast" rate that can be terminated by ATP in the first chamber, occurs only when the intervals between events in the first chamber are between a minimum and maximum predetermined limits, which limits may be programmable and preferably are 375 ms (corresponding to ventricular fibrillation and 600 ms (corresponding to a sinus rhythm), respectively. Preferably, some historical average of recent fast and slow RR intervals is used for this evaluation.

In yet another aspect of the invention, the cardiac rhythms are sorted further when there is a determined stability in the first chamber and a determined conduction stability, by identifying the occurrence of an acceleration of the frequency in the first chamber which is greater than a predetermined acceleration limit, identifying the occurrence of a dissociation of conduction between the two chambers during the detection of the acceleration, and determining that the tachyarrhythmia is susceptible to be terminated by a stimulation in the first chamber when there is both acceleration and dissociation. The step of determining if the tachyarrhythmia is susceptible to be terminated determines terminability only when it is also determined that there is a determined 1:1 association ratio, and preferably applies ATP to a tachyarrhythmia determined to be susceptible to termination by stimulation. It should be understood that the acceleration criterion is applied only after a determined 1:1 association ratio. A determined 1:1 association ratio may for purposes of this disclosure be other than a mathematic 1:1 ratio, as previously noted.

BRIEF DESCRIPTION OF THE DRAWING

Further features of the invention, its nature and various advantages will be more apparent from the accompanying drawing, and the following detailed description of the invention, in which the drawing is a flowchart illustrating a routine implementating the decision logic in accordance with the invention.

DETAILED DESCRIPTION OF THE INVENTION

Figure 1:
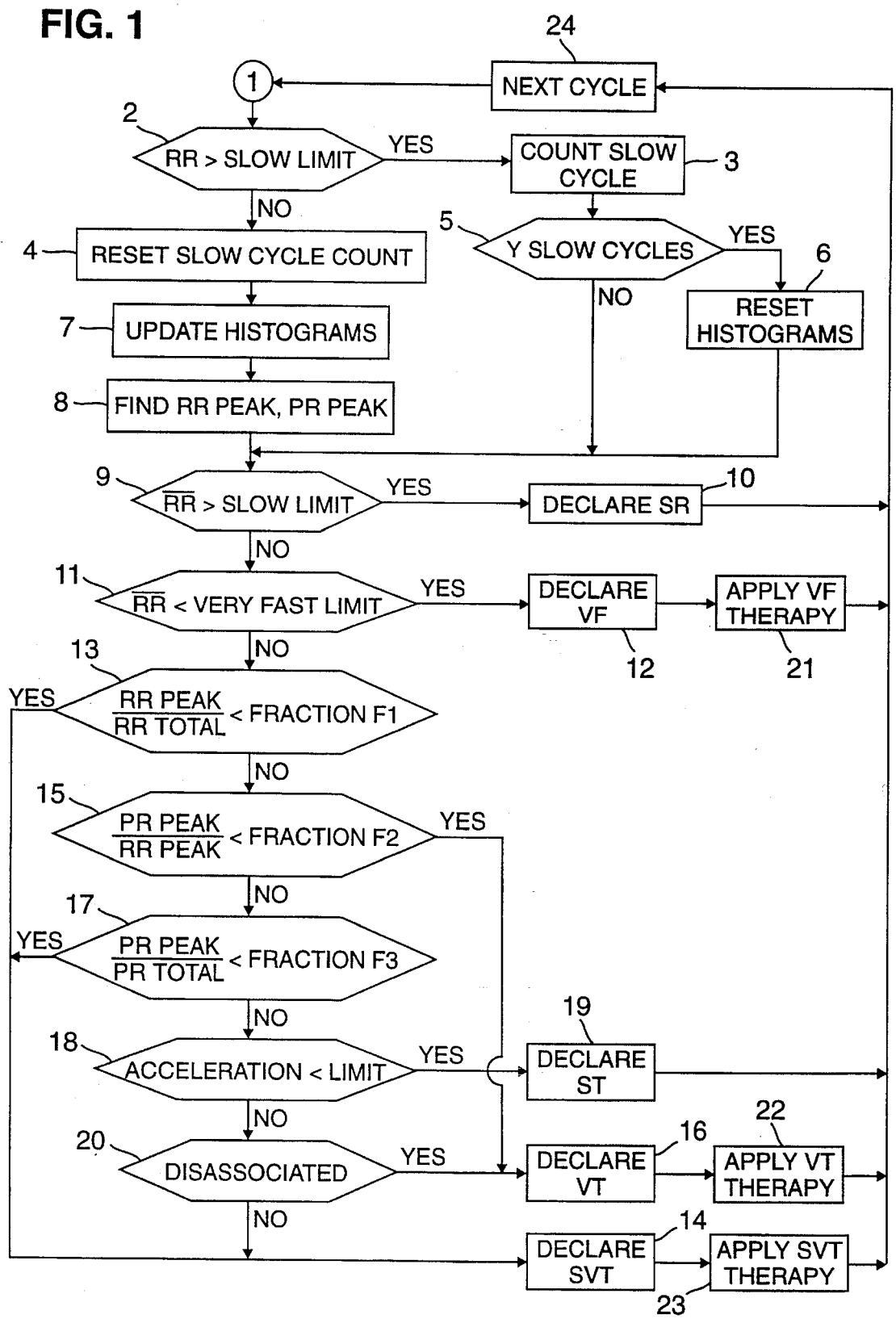

Referring to the drawing, an illustration of an embodiment of the present invention is applied to determining when tachyarrhythmias are pace-terminable in the ventricle. As explained above, the invention can equally well be applied to determining when tachyarrhythmias are pace-terminable in the atrium.

Referring to the drawing, there is depicted a flowchart showing the decision path of a routine in accordance with the invention, with entry point 1, following the detection of an R-wave (i.e., a ventricular beat). At step 2 the routine determines if the RR interval length exceeds a preset "slow" limit (which may be programmable and is preferably approximately 600 ms), in which case the rhythm is probably a sinus rhythm SR. (A large interval corresponds to a slow cardiac rate). If yes, a slow cycle counter is incremented at 3. At 5, the slow cycle counter count is tested, and if the count reaches a preset number Y of consecutive slow cycles (where Y may be programmable and is preferably approximately 16 cycles), then each bin of the histograms is reset at step 6. This action is taken based on the information previously stored being no longer current. Thus, in this manner, when the RR interval is greater than the slow limit (step 2), the routine does not perform the time- and power-consuming steps of updating and analyzing the histograms, which it does perform as described below, when a tachyarrhythmia might be present. This reduces battery consumption which is an important advantage for an implantable antitachycardia device.

If the RR interval does not exceed the slow interval limit at step 2, then the slow cycle counter is reset at 4. Then, at step 7 the method updates an RR interval histogram and a PR interval histogram. In this regard, in the RR interval histogram, when the bin corresponding to the RR interval just elapsed is incremented, the bin that was incremented Z fast cycles ago (where Z may be programmable and is preferably 16), if any, is decremented. Similarly, in the PR interval histogram, the bin corresponding to each of the PR intervals detected in the last RR cycle, one for each detected P-wave, is incremented, and any bins which were incremented Z fast cycles ago, are decremented. In this manner, the histograms store information for the Z most recent cycles where the ventricular rate was faster than the slow limit. A count of the total number of RR intervals in the RR histogram is maintained, referred to as the RR total (or auto-correlation total), and a count of the total number of PR intervals in the PR histogram is maintained, referred to as the PR (or cross-correlation total). It is noted that when sorting rhythms originating in the atrium, a PP interval histogram and RP interval histogram are used in a parallel manner. The histogram for cardiac intervals also is referred to as the auto-correlation histogram, and the histogram for the conduction intervals also is referred to as the cross-correlation histogram.

At step 8, the routine determines the auto-correlation peak (also called the RR peak), and the cross-correlation peak (also called the PR peak). Each peak is determined by scanning all the bins of the particular histogram with a window, whose width may be programmable and is preferably 64 ms. In this regard, the window is placed at one end of the histogram range and the number of events in the bins within the window are counted. The window is then shifted through the histogram range, one bin at a time. Each time the window is moved by one bin, the total of the counts in all the bins in the window is calculated. The highest total count of all of the possible window positions is saved as the maximum or peak count. In this manner, the peak is the maximum total number of counts in any set of contiguous bins which fit inside the window.

At step 9 an averaged RR interval is compared to a preset "slow" limit, which may be programmable and is preferably approximately 600 ms. If the average RR interval is longer than the "slow" limit, the routine declares an SR condition at step 10 and the routine returns to wait for the next cycle at point 24, for subsequent cardiac event processing beginning at point 1.

At step 11 the averaged RR interval is compared to a preset "very fast" limit (which may be programmable and is preferably approximately 375 ms). If the average RR interval is shorter than the "very fast" limit, a VF condition is declared at step 12. Optionally, therapy to revert ventricular fibrillation is applied at step 21 in response to a declared condition VF at step 12.

The averaged RR interval is used at steps 9 and 11 to prevent isolated premature beats, unsensed beats, and bursts of electrical noise, from grossly affecting the decision. It is maintained separately from the histogram and may be an average of the last 16 determined intervals. In alternate embodiments, a moving average, low-pass filter, X out of Y detector, or other conventional filter could be used.

At step 13, the RR peak is divided by RR total. If the quotient is less than a preset fraction F1 (which may be programmable and is preferably approximately 75%) then it is declared unlikely that there is conduction on a fixed pathway from one ventricular sensed event causing the next. Accordingly, the device declares an SVT condition at step 14.

At step 15, the PR peak is divided by the RR peak. If the quotient is less than a preset fraction F2 (which may be programmable and is preferably approximately 75%) then it is declared less likely that there is conduction from the atrium to the ventricle than from the ventricle to the ventricle. Accordingly, the device declares a VT condition at step 16.

In an alternative embodiment, at step 15 the PR peak is divided by RR total (not shown). The decision is then made based on absolute stability of the PR interval, rather than on the relative stability of the PR interval, as compared with the RR interval.

At step 17, the PR peak is divided by PR total. If the quotient is less than a preset fraction F3 (which may be programmable and is preferably approximately 75%) then conduction from atrium to ventricle is many:1, and there is little risk of confusing this with conduction from ventricle to atrium. Accordingly, the device declares an SVT condition at step 14.

As an alternative, when the number of events counted in the second chamber is divided by the number of events counted in the first chamber is greater than a predetermined fraction of, for example, 1.33, or less than a fraction of, for example, 0.66, an association of many:1 is declared.

At step 18, there is RR stability and PR stability, with 1:1 conduction. This situation could correspond to an atrial tachyarrhythmia conducted to the ventricle, or a ventricular tachyarrhythmia conducted to the atrium. However, the process must apply another criterion to determine the origin of the tachyarrhythmia. Preferably, the criterion applied is an acceleration criterion in which the ventricular rate acceleration is compared to a preset limit, which may be programmable, and is preferably approximately 25%. If the rate does not exceed the limit, then it is declared likely that this is sinus tachycardia, and accordingly the device declares an ST condition at step 19.

At step 20, it is determined if there was atrioventricular disassociation at the onset of ventricular acceleration. If there was, then it is declared likely that the tachyarrhythmia had a ventricular origin, and the device declares a VT condition at step 16. If there was not, then the device declares an SVT condition at 14. One method for determining association requires, for example, that the conduction intervals for the accelerated beat and its predecessor both fall within a predetermined range corresponding to physiological conduction, e.g., 30 ms to 300 ms for atrio-ventricular conduction.

As illustrated in the drawing, in accordance with a preferred embodiment of the invention, and according to the declared cardiac condition, the appropriate therapy at steps 21, 22, or 23 is delivered by the device. Thereafter, the routine returns to step 24 and waits for the next cycle, and then resumes analysis at entry point 1.

After the histograms are reset at step 6, the routine can suspend declaring the type of rhythm present until a preset number of cycles have been used to update the histograms. The preset number may be programmable, and is preferably approximately 8.

The system embodying the present invention includes a device capable of the creation and maintenance of the appropriate histograms in suitable data storage devices and a software program or solid state finite state machine for the automatic computation of the RR and PR intervals (recalling that alternately and additionally the intervals may be based on atrial events, e.g., PP intervals and RP intervals), and the processing of the intervals to make the tests and determinations regarding stability, conduction instability, association, and acceleration, and the storage of the various predetermined parameters, constants, and fractions. More preferably, such a device also includes the detection of atrial and ventricular beats and the measuring of these beats and the noted intervals are performed by conventional devices having atrial and ventricular sense amplifiers, signal conditioning circuits, analog-to-digital conversion circuits, and suitable memory and registers for time-based digital data processing and manipulation as are now common in cardiac pacemaker, defibrillator and cardioverter devices. Representative electronic circuits for acquiring the cardiac signals and determining the PR and RR intervals (and PP and RP intervals) are those found in the series of dual chamber pacemakers available from Ela Medical, Montrouge, France, offered under the CHORUS trademark. The present invention is preferably implemented in software instructions loadable or loaded in memory for operating a microprocessor to process acquired cardiac signals, and is specifically applied following acquisition of the cardiac electric signals by conventional sense amplifiers, more preferably after the acquired signals have been conditioned and converted to a digital form.

One skilled in the art will appreciate that the present invention can be practiced by other than the preferred embodiments, which are presented for purposes of illustration and not of limitation. Numerous other modifications may be made and other arrangements may be devised without departing from the spirit and scope of the present invention.

We claim:

1. A method of analyzing a patient's cardiac activity comprising the steps of:

(a) detecting cardiac events in the atrium and the ventricle;

(b) determining an interval between each detected event in a first chamber, each interval having a time length, said first chamber being one of the atrium and the ventricle;

(c) determining a conduction interval between a sensed cardiac event in the first chamber and a preceding sensed cardiac event in the second chamber, each conduction interval having a time length, the second chamber being the other of the atrium and ventricle;

(d) forming an auto-correlation histogram of determined intervals in said first chamber corresponding to a cardiac cycle in the first chamber that is above a sinus rhythm;

(e) forming a cross-correlation histogram of determined conduction intervals corresponding to a cardiac cycle in the first chamber that is above a sinus rhythm;

(f) processing the auto-correlation histogram by
      (i) scanning the auto-correlation histogram with a stability window, determining the number of intervals in the stability window for each position of the stability window in the auto-correlation histogram, and determining the maximum number of intervals within said stability window of all of the possible positions of the stability window,
      (ii) determining an auto-correlation peak count as said determined maximum number of intervals that satisfy the stability window, and
      (iii) providing an auto-correlation total corresponding to the number of the determined intervals in the auto-correlation histogram;

(g) processing the cross-correlation histogram by
      (i) scanning the cross-correlation histogram with a conduction time window, determining the number of intervals in the conduction time window for each position of the conduction time window in the cross-correlation histogram and determining the maximum number of determined conduction intervals within said conduction time window of all of the possible positions of said conduction time window,
      (ii) determining a cross-correlation peak count as the determined number of maximum determined conduction intervals that satisfy the conduction time window, and
      (iii) providing a cross-correlation total corresponding to the number of the determined conduction intervals in the cross-correlation histogram; and (h) determining whether the patient's cardiac events correspond to a tachyarrhythmia that is terminable by a stimulation pulse in the first chamber based on the determined auto-correlation peak and the determined cross-correlation peak.

2. The method of claim 1 wherein step (d) further comprises providing a first plurality of first bins, each first bin corresponding to a different range of interval time lengths, and sorting the determined intervals into said first bins according to the time lengths of said determined intervals, and wherein step (e) further comprises providing a second plurality of second bins, each second bin corresponding to a different range of interval time lengths, and sorting the determined conduction intervals lengths into said second bins according to the time lengths of said determined conduction intervals.

3. The method of claim 2 wherein providing said first plurality of first bins further comprises providing said first bins with contiguous ranges of time intervals over a first time range, and wherein providing said second plurality of second bins further comprises providing said second bins with contiguous ranges of time intervals over a second time range.

4. The method of claim 2 wherein the scanning step (f)(i) further comprises providing said stability window with a time length corresponding to a third plurality of contiguous first bins, the third plurality being less than the first plurality, and wherein the scanning step (g)(i) further comprises providing said conduction time window with a time length corresponding to a fourth plurality of contiguous second bins, the fourth plurality being less than the second plurality.

5. The method of claim 4 wherein providing said first and second bins further comprises providing each first and second bin with a time length range of approximately 16 ms, wherein providing said stability window further comprises providing said stability window with a time length of approximately 64 ms, and wherein providing said conduction time window further comprises providing said conduction time window with a time length of approximately 64 ms.

6. The method of claim 2 wherein step (d) further comprises sorting detected intervals having an interval time length in the range of from 125 ms to 600 ms and wherein step (e) further comprises sorting detected conduction intervals having a conduction interval time length in the range of from 16 ms to 500 ms.

7. The method of claim 1 wherein the scanning step (f)(i) further comprises providing said stability window with a time length corresponding to a subset of said auto-correlation histogram and wherein the scanning step (g)(i) further comprises providing said conduction time window with a time length corresponding to a subset of said cross-correlation histogram.

8. The method of claim 1 wherein steps (d) and (e) further comprise adjusting the contents of the auto-correlation histogram and the cross-correlation histogram respectively to correspond to sensed cardiac activity from a predetermined number of cardiac cycles in the first chamber, including the determined interval and any determined conduction intervals in response to the sensed cardiac events of a recent cardiac cycle and deleting from the histograms the determined interval and any determined conduction intervals of sensed cardiac events of a prior cardiac cycle in the first chamber, the prior cardiac cycle occurring more than said predetermined number of cardiac cycles preceding the recent cardiac cycle, and wherein the steps (f) and (g) further comprise processing the adjusted auto-correlation and cross-correlation histograms respectively.

9. The method of claim 8 wherein adjusting the contents of the auto-correlation and cross-correlation histograms respectively further comprise forming said histograms based on the determined intervals and determined conduction intervals for the 16 most recent cardiac cycles in the first chamber that are above a sinus rhythm, respectively.

10. The method of claim 1 wherein step (b) further comprises determining whether the determined interval exceeds a preselected limit corresponding to a sinus rhythm limit and not performing steps (c) through (g) in response to said determined interval being longer than said preselected limit.

11. The method of claim 10 further comprising determining when the determined intervals exceeds the preselected limit for more than a first predetermined number of cardiac cycles and, in response thereto:

(i) resetting said auto-correlation histogram and said cross-correlation histogram;

(ii) resuming steps (c) through (e) subsequent to step (i), and (iii) resuming steps (a) through (g) following the occurrence of determined intervals and conduction intervals corresponding to a second predetermined number of cardiac cycles in the first chamber that are above the sinus rhythm subsequent to step (i).

12. The method of claim 11 wherein step (b) further comprises providing said first predetermined number of cardiac cycles as sixteen cardiac cycles and providing said second predetermined number of cardiac cycles as eight cardiac cycles.

13. The method of claim 1 wherein step (h) further comprises determining the existence of stability in the first chamber in response to the quotient of the auto-correlation peak divided by the auto-correlation total exceeding a first fraction, and declaring the tachyarrhythmia not terminable by a stimulation pulse in the first chamber in the absence of stability in the first chamber.

14. The method of claim 1 wherein step (h) further comprises determining the existence of stability in the first chamber in response to the quotient of the auto-correlation peak divided by the auto-correlation total exceeding a first fraction, determining the existence of conduction instability for conduction from the second chamber to the first chamber in response to the quotient of the cross-correlation peak divided by the auto-correlation total not exceeding a second fraction, and declaring the tachyarrhythmia terminable by a stimulation pulse in the first chamber in response to there being stability in the first chamber and conduction instability.

15. The method of claim 1 wherein step (h) further comprises determining the existence of stability in the first chamber in response to the quotient of the auto-correlation peak divided by the auto-correlation total exceeding a first fraction, determining the existence of conduction instability for conduction from the second chamber to the first chamber in response to the quotient of the cross-correlation peak divided by the auto-correlation peak not exceeding a second fraction, and declaring the tachyarrhythmia terminable by a stimulation pulse in the first chamber in response to there being stability in the first chamber and conduction instability.

16. The method of claim 1 wherein step (h) further comprises:

determining the existence of stability in the first chamber in response to the quotient of the auto-correlation peak divided by the auto-correlation total exceeding a first fraction;

determining the existence of conduction stability for conduction from the second chamber to the first chamber in response to the quotient of the cross-correlation peak divided by the auto-correlation total exceeding a second fraction;

determining an association ratio of the detected events in the first chamber and the second chamber; and in response to a determined 1:1 association ratio, (i) determining an acceleration of the determined intervals and identifying the occurrence of an acceleration of rate in the first chamber exceeding a preselected acceleration limit, and (ii) determining the occurrence of a disassociation of conduction between the first and second chambers at the onset of said identified acceleration; and declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

17. The method of claim 16 wherein determining the association ratio further comprises comparing the quotient of the cross-correlation peak divided by the cross-correlation total to a preset fraction, and determining a 1:1 association ratio if said quotient is greater than said preset fraction.

18. The method of claim 16 wherein determining the association ratio further comprises determining a 1:1 association ratio in response to the quotient of the auto-correlation total divided by the cross-correlation total being in a range of from 0.66 to 1.33.

19. The method of claim 1 wherein step (h) further comprises:

determining the existence of stability in the first chamber in response to the quotient of the auto-correlation peak divided by the auto-correlation total exceeding a first fraction;

determining the existence of conduction stability for conduction from the second chamber to the first chamber in response to the quotient of the cross-correlation peak divided by the auto-correlation peak exceeding a second fraction;

determining an association ratio of the detected events in the first chamber and the second chamber;

in response to a determined 1:1 association ratio, (i) determining an acceleration of the determined intervals and identifying the occurrence of an acceleration of rate in the first chamber exceeding a preselected acceleration limit, and (ii) determining the occurrence of a disassociation of conduction between the first and second chambers at the onset of said identified acceleration; and declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

20. The method of claim 19 wherein determining the association ratio further comprises comparing the quotient of the cross-correlation peak divided by the cross-correlation total to a preset fraction, and determining a 1:1 association ratio if said quotient is greater than said preset fraction.

21. The method of claim 19 wherein determining the association ratio further comprises determining a 1:1 association ratio in response to the quotient of the auto-correlation total divided by the cross-correlation total being in a range of from 0.66 to 1.33.

22. The method of claims 1, 15, 16, or 19 further comprising:

(i) applying antitachycardia pacing to the first chamber in response to a tachyarrhythmia that is determined terminable by a stimulation pulse.

23. A method of analyzing a patient's cardiac activity comprising the steps of:

(a) sensing cardiac events in the atrium and the ventricle;

(b) processing the sensed cardiac events including the steps of
  (i) determining an interval between each detected event in a first chamber corresponding to a cardiac cycle, each interval having a time length, said first chamber being one of the atrium and the ventricle;
  (ii) selecting the determined intervals corresponding to a plurality of cardiac cycles above a sinus rhythm, providing a first total as a count of said selected determined intervals and determining whether said determined intervals satisfy a stability criterion;
  (iii) determining a first peak count of the determined intervals that satisfy said stability criterion;
  (iv) determining a conduction interval between a sensed cardiac event in the first chamber and each preceding sensed cardiac event in the second chamber for the plurality of cardiac cycles, each conduction interval having a time length, the second chamber being the other of the atrium and ventricle, and providing a second total as a count of said determined conduction intervals;
  (v) determining whether each conduction interval time length is within a conduction time stability criterion; and
  (vi) determining a second peak count of the determined conduction intervals that are within the conduction time stability criterion; and (c) determining whether the patient's processed cardiac events correspond to a tachyarrhythmia that is terminable by a stimulation pulse in the first chamber based on the determined first and second peaks.

24. The method of claim 23 wherein steps (b) (ii) and (iii) further comprise:

forming a histogram of the selected determined intervals in said first chamber for a range of interval lengths;

providing the first total as corresponding to the number of the intervals in the histogram; and scanning the histogram with a stability window having an interval that is a subset of the histogram interval length range, determining the number of intervals in the stability window for each position of the stability window in the histogram, and determining said first peak as the maximum number of intervals within said stability window for all possible positions of the stability window in the auto-correlation histogram.

25. The method of claim 24 wherein forming the histogram further comprises providing a plurality of bins, each bin corresponding to different range of interval time lengths, and sorting the selected determined intervals lengths into said bins according to the time lengths of said intervals.

26. The method of claim 25 wherein providing said plurality of bins further comprises providing each said bin with a time length range of approximately 16 ms and providing said bins with contiguous ranges of time intervals, and wherein the scanning step further comprises providing said stability window with a time length corresponding to a plurality of contiguous bins.

27. The method of claim 25 wherein forming said histogram further comprises sorting selected detected intervals having an interval time length in the range of from 125 ms to 600 ms.

28. The method of claim 24 wherein step (b) further comprises adjusting the plurality of cardiac cycles processed by including sensed cardiac events corresponding to a recent cardiac cycle in the first chamber above the sinus rhythm and deleting previously sensed cardiac events corresponding to cardiac cycles in the first chamber above the sinus rhythm occurring more than a predetermined number of cardiac cycles preceding the recent cardiac cycle, and wherein the step of forming the histogram further comprises updating the histogram so that the histogram contains the selected determined intervals for said predetermined number of cardiac cycles, and wherein said steps of providing said total and scanning the histogram further comprise performing said providing and scanning steps based on said updated histogram.

29. The method of claim 28 wherein adjusting the plurality of cardiac cycles processed further comprises processing the sensed cardiac activity for the 16 most recent cardiac cycles in the first chamber above the sinus rhythm.

30. The method of claim 24 wherein step (b)(i) further comprises determining whether the determined interval exceeds a preselected limit corresponding to a sinus rhythm limit and not performing the processing of steps (b)(ii) through (b)(vi) and (c) in response to said determined interval being longer than said preselected limit.

31. The method of claim 30 further comprising determining when the determined intervals exceed the preselected limit for more than said plurality of cardiac cycles and, in response thereto, resetting said histogram, and selecting for processing cardiac events sensed during a second time period corresponding to a second plurality of cardiac cycles in the first chamber above a sinus rhythm, said second time period being later in time than said first time.

32. The method of claim 23 wherein steps (b)(iv), (v) and (vi) further comprise:

forming a histogram of the determined conduction intervals for a range of interval lengths;

providing the second total as corresponding to the number of the conduction intervals in the cross-correlation histogram; and scanning the histogram with a conduction time window having an interval that is a subset of the histogram range, determining the number of conduction intervals in the conduction time window for each position of the conduction time window in the histogram, and determining said second peak as the maximum number of conduction intervals within said conduction time window for all possible positions of said conduction time window in the histogram.

33. The method of claim 32 wherein forming the histogram further comprises providing a plurality of bins, each bin having a different range of time interval lengths, and sorting the determined conduction intervals lengths into said bins according to the time lengths of said conduction intervals.

34. The method of claim 33 wherein providing said plurality of bins further comprises providing each said bin with a time length range of approximately 16 ms, providing said bins with contiguous ranges of time intervals, and wherein the scanning step further comprises providing said conduction time window with a time length corresponding to a plurality of contiguous bins.

35. The method of claim 33 wherein forming said histogram further comprises sorting detected conduction intervals having a conduction interval time length in the range of from 16 ms to 500 ms.

36. The method of claim 32 wherein step (b) further comprises adjusting the plurality of cardiac cycles processed by including sensed cardiac events corresponding to a recent cardiac cycle in the first chamber above the sinus rhythm and deleting previously sensed cardiac events corresponding to prior cardiac cycles in the first chamber above the sinus rhythm occurring more than a predetermined number of cardiac cycles preceding the recent cardiac cycle, and wherein the step of forming the histogram further comprises updating the histogram so that the histogram contains the determined conduction intervals for said predetermined number of cardiac cycles, and wherein said steps of providing said second total and scanning the histogram further comprise performing said providing and scanning steps based on said updated histogram.

37. The method of claim 36 wherein adjusting the plurality of cardiac cycles processed further comprises processing the sensed cardiac activity for the 16 most recent cardiac cycles in the first chamber above the sinus rhythm.

38. The method of claim 32 wherein step (b)(i) further comprises determining whether the determined interval exceeds a preselected limit corresponding to a sinus rhythm limit and not performing the processing of steps (b)(ii) through (b)(vi) and (c) in response to said determined interval being longer than said preselected limit.

39. The method of claim 38 further comprising determining when the determined intervals exceed the preselected limit for more than said plurality of cardiac cycles and, in response thereto, resetting said histogram, and selecting for processing cardiac events sensed during a second time period corresponding to a second plurality of cardiac cycles in the first chamber above the sinus rhythm, said second time being later in time than said first time.

40. The method of claim 23 wherein step (b) further comprises adjusting the plurality of cardiac cycles processed by including sensed cardiac events corresponding to a recent cardiac cycle in the first chamber above the sinus rhythm and deleting previously sensed cardiac events corresponding to cardiac cycles in the first chamber above the sinus rhythm occurring more than said plurality of cardiac cycles preceding the recent cardiac cycle.

41. The method of claim 40 wherein adjusting the plurality of cardiac cycles processed further comprises processing the sensed cardiac activity for the 16 most recent cardiac cycles in the first chamber above the sinus rhythm.

42. The method of claim 23 wherein step (b)(i) further comprises determining whether the determined interval exceeds a preselected limit corresponding to a sinus rhythm limit and not performing the processing of steps (b)(ii) through (b)(vi) and (c) in response to said determined interval being longer than said preselected limit.

43. The method of claim 42 wherein step (b)(i) further comprises providing said preselected limit to be an interval of approximately 600 ms.

44. The method of claim 42 further comprising determining when the determined intervals exceeds the preselected limit for more than said plurality of cardiac cycles and, in response thereto, selecting for processing cardiac events sensed during a second time period corresponding to a second plurality of cardiac cycles in the first chamber above a sinus rhythm, said second time period being later in time than said first time.

45. The method of claim 42 wherein step (b) further comprises providing said plurality of cardiac cycles as sixteen cardiac cycles.

46. The method of claims 24 or 32 further comprising forming an average of a plurality of determined intervals and sorting rhythms only when the determined average interval time length falls between a preset lower limit and a preset upper limit defining a likely tachycarrhythmia range.

47. The method of claim 46 where the preset lower limit is approximately 375 ms and the preset upper limit is approximately 600 ms.

48. The method of claims 23, 24 or 32 wherein step (c) further comprises determining the existence of stability in the first chamber in response to the quotient of the first peak divided by the first total exceeding a first fraction, and declaring the tachyarrhythmia not terminable by a stimulation pulse in the first chamber in the absence of stability in the first chamber.

49. The method of claims 23, 24, or 32 wherein step (c) further comprises determining the existence of stability in the first chamber in response to the quotient of the first peak divided by the first total exceeding a first fraction, determining the existence of conduction instability for conduction from the second chamber to the first chamber in response to the quotient of the second peak divided by the first total not exceeding a second fraction, and declaring the tachyarrhythmia terminable by a stimulation pulse in the first chamber in response to there being stability in the first chamber and conduction instability.

50. The method of claims 23, 24 or 32 wherein step (c) further comprises determining the existence of stability in the first chamber in response to the quotient of the first peak divided by the first total exceeding a first fraction, determining the existence of conduction instability for conduction from the second chamber to the first chamber in response to the quotient of the second peak divided by the first peak not exceeding a second fraction, and declaring the tachyarrhythmia terminable by a stimulation pulse in the first chamber in response to there being stability in the first chamber and conduction instability.

51. The method of claims 23, 24 or 32 wherein step (c) further comprises:

determining the existence of stability in the first chamber in response to the quotient of the first peak divided by the first total exceeding a first fraction;

determining the existence of conduction stability for conduction from the second chamber to the first chamber in response to the quotient of the second peak divided by the first total exceeding a second fraction;

determining an association ratio of the detected events in the first chamber and in the second chamber; and in response to determined 1:1 association ratio, (i) determining an acceleration of the determined intervals and identifying the occurrence of an acceleration of rate in the first chamber exceeding a preselected acceleration limit, and (ii) determining the occurrence of a disassociation of conduction between the first and second chambers at the onset of said identified acceleration; and declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

52. The method of claim 51 wherein determining the association ratio further comprises comparing the quotient of the second peak divided by the second total to a present fraction, and determining a 1:1 association ratio if said quotient is greater than said preset fraction.

53. The method of claim 51 wherein determining the association ratio further comprises determining a 1:1 association ratio in response to the quotient of the first total divided by the second total being in a range of from 0.66 to 1.33.

54. The method of claims 23, 24 or 32 wherein step (c) further comprises:

determining the existence of stability in the first chamber in response to the quotient of the first peak divided by the first total exceeding a first fraction;

determining the existence of conduction stability for conduction from the second chamber to the first chamber in response to the quotient of the second peak divided by the first peak exceeding a second fraction;

determining an association ratio of the detected events in the first chamber and the second chamber; and in response to a determined 1:1 association ratio, (i) determining an acceleration of the determined intervals and identifying the occurrence of an acceleration of rate in the first chamber exceeding a preselected acceleration limit, and (ii) determining the occurrence of a disassociation of conduction between the first and second chambers at the onset of said identified acceleration; and declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

55. The method of claim 54 wherein determining the association ratio further comprises comparing the quotient of the second peak divided by the second total to a present fraction, and determining a 1:1 association ratio if said quotient is greater than said preset fraction.

56. The method of claim 54 wherein determining the association ratio further comprises declaring a 1:1 association ratio in response to the quotient of the first total divided by the second total being in a range of from 0.66 to 1.33.

57. The method of claims 23, 24, or 32, further comprising:

(d) applying antitachycardia pacing to the first chamber in response to a tachyarrhythmia that is determined terminable by a stimulation pulse.

58. Apparatus for analyzing a patient's cardiac activity comprising:

means for sensing cardiac events in the atrium and the ventricle;

means for processing the sensed cardiac events comprising first means for determining an interval between each detected event corresponding to a cardiac cycle in a first chamber, each interval having a time length, said first chamber being one of the atrium and the ventricle;

second means for selecting the determined intervals above a sinus rhythm and corresponding to a plurality of cardiac cycles, determining whether the selected determined intervals satisfy a stability criterion;

third means for determining a first peak count of the selected determined intervals that satisfy said stability criterion;

first count means for providing a first total of the number of selected determined intervals;

fourth means for determining a conduction interval between a sensed cardiac event in the first chamber and each preceding sensed cardiac event in the second chamber for the plurality of cardiac cycles, each determined conduction interval having a time length, the second chamber being the other of the atrium and ventricle;

fifth means for determining whether each determined conduction interval time length is within a conduction time stability criterion;

sixth means for determining a second peak count of the determined conduction intervals that are within the conduction time stability criterion; and second count means for providing a second total as a count of said determined conduction intervals; and seventh means for determining whether the patient's processed cardiac events correspond to a tachyarrhythmia that is terminable by a stimulation pulse in the first chamber based on the determined first and second peaks.

59. The apparatus of claim 58 wherein the second and third determining means further comprise:

a histogram of the selected determined intervals in said first chamber for a range of interval lengths;

a stability window having an interval that is a subset of the histogram interval length range; and means for scanning the histogram with the stability window and determining said first peak as the maximum number of determined intervals within said stability window for all possible positions of the stability window in the auto-correlation histogram, wherein first total corresponds to the number of the determined intervals in the histogram.

60. The apparatus of claim 59 wherein the histogram further comprises a plurality of bins, each bin corresponding to different range of interval time lengths, and the selected determined intervals lengths are sorted into said bins according to the time lengths of said intervals.

61. The apparatus of claim 60 wherein said plurality of bins further comprises contiguous bins, each bin having a time length range of approximately 16 ms, and wherein the stability window has a time length corresponding to a plurality of contiguous bins.

62. The apparatus of claim 58 wherein the fifth and sixth determining means further comprise:

a histogram of the determined conduction intervals for a range of interval lengths;

a conduction time window having an interval that is a subset of the histogram range; and means for scanning the histogram with the conduction time window and determining said second peak as the maximum number of determined conduction intervals within said conduction time window for all possible positions of said conduction time window in the histogram, wherein the second total corresponds to the number of the determined conduction intervals in the histogram.

63. The apparatus of claim 62 wherein the histogram further comprises a plurality of bins, each bin having a different range of time interval lengths, and the determined conduction intervals lengths are sorted into said bins according to the time lengths of said determined conduction intervals.

64. The apparatus of claim 63 wherein said plurality of bins further comprises contiguous bins, each bin having a time length range of approximately 16 ms, and wherein the conduction time window has a time length corresponding to a plurality of contiguous bins.

65. The apparatus of claim 59 or 62 wherein the processing means further comprises means for including sensed cardiac events corresponding to a recent cardiac cycle in the first chamber above the sinus rhythm and deleting previously sensed cardiac events corresponding to cardiac cycles in the first chamber above the sinus rhythm occurring more than a predetermined number of cardiac cycles preceding the recent cardiac cycle, and further comprises means for updating the histogram so that the histogram contains the determined intervals for said predetermined number of cardiac cycles.

66. The apparatus of claims 59 or 62 wherein the first determining means further comprises eighth means for determining whether the determined interval exceeds a preselected limit corresponding to a sinus rhythm limit wherein said second, third, fourth, fifth and sixth determining means do not operate in response to said eighth determining means determining that the determined interval is longer than said preselected limit.

67. The apparatus of claim 66 wherein the eighth determining means determines when the determined intervals exceeds the preselected limit for more than said plurality of cardiac cycles and, in response thereto, resets said histogram, and selects for processing cardiac events sensed during a second time corresponding to a second plurality of cardiac cycles in the first chamber above a sinus rhythm, said second time being later in time than said first time.

68. The apparatus of claim 58 wherein the processing means further comprises means for adjusting the plurality of cardiac cycles processed by including sensed cardiac events corresponding to a recent cardiac cycle in the first chamber above the sinus rhythm and deleting previously sensed cardiac events corresponding to cardiac cycles in the first chamber above the sinus rhythm occurring more than said plurality of cardiac cycles preceding the recent cardiac cycle.

69. The apparatus of claim 58 wherein said first determining means further comprises eighth means for determining whether the determined interval exceeds a preselected limit corresponding to a sinus rhythm limit, wherein said second, third, fourth, fifth and sixth determining means do operate not in response to the eighth determining means determining that said determined interval is longer than said preselected limit.

70. The apparatus of claim 69 wherein said preselected limit is approximately 600 ms.

71. The apparatus of claims 59 or 62 further comprising means for determining an average of a plurality of determined intervals and means for sorting intervals to form said histogram only when the determined average interval time length falls between a preset lower limit and a preset upper limit defining a likely tachyarrhythmia range.

72. The apparatus of claims 58, 59 or 62 wherein the seventh determining means further comprises means for determining the existence of stability in the first chamber in response to the quotient of the first peak divided by the first total exceeding a first fraction, and means for declaring the tachyarrhythmia not terminable by a stimulation pulse in the first chamber in the absence of stability in the first chamber.

73. The apparatus of claims 58, 59 or 62 wherein the seventh determining means further comprises means for determining the existence of stability in the first chamber in response to the quotient of the first peak divided by the first total exceeding a first fraction, means for determining the existence of conduction instability for conduction from the second chamber to the first chamber in response to the quotient of the second peak divided by the first total not exceeding a second fraction, and means for declaring the tachyarrhythmia terminable by a stimulation pulse in the first chamber in response to there being stability in the first chamber and conduction instability.

74. The apparatus of claims 58, 59 or 62 wherein the seventh determining means further comprises means for determining the existence of stability in the first chamber in response to the quotient of the first peak divided by the first total exceeding a first fraction, means for determining the existence of conduction instability for conduction from the second chamber to the first chamber in response to the quotient of the second peak divided by the first peak not exceeding a second fraction, and means for declaring the tachyarrhythmia terminable by a stimulation pulse in the first chamber in response to there being stability in the first chamber and conduction instability.

75. The apparatus of claims 58, 59 or 62 wherein the seventh determining means further comprises:

means for determining the existence of stability in the first chamber in response to the quotient of the first peak divided by the first total exceeding a first fraction;

means for determining the existence of conduction stability for conduction from the second chamber to the first chamber in response to the quotient of the second peak divided by the first total exceeding a second fraction;

means for determining an association ratio of the detected events in the first chamber and in the second chamber;

means, responsive to a determined 1:1 association ratio, for determining an acceleration of the determined intervals and identifying the occurrence of an acceleration of rate in the first chamber exceeding a preselected acceleration limit;

means, responsive to a determined 1:1 association ratio for determining the occurrence of a disassociation of conduction between the first and second chambers at the onset of said identified acceleration; and means for declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

76. The apparatus of claim 75 wherein the association ratio determining means further comprises means for determining a 1:1 association ratio in response to the quotient of the second peak divided by the second total being greater than a preset fraction.

77. The apparatus of claim 75 wherein the association ratio determining means further comprises means for determining a 1:1 association ratio in response to the quotient of the first total divided by the second total being in a range of from 0.66 to 1.33.

78. The apparatus of claims 58, 59 or 62 wherein the seventh determining means further comprises:

means for determining the existence of stability in the first chamber in response to the quotient of the first peak divided by the first total exceeding a first fraction;

means for determining the existence of conduction stability for conduction from the second chamber to the first chamber in response to the quotient of the second peak divided by the first peak exceeding a second fraction;

means for determining an association ratio of the detected events in the first chamber and the second chamber;

means, responsive to a determined 1:1 association ratio, for determining an acceleration of the determined intervals and identifying the occurrence of an acceleration of rate in the first chamber exceeding a preselected acceleration limit, means for determining the occurrence of a disassociation of conduction between the first and second chambers at the onset of said identified acceleration; and means for declaring the tachyarrhythmia terminable by a stimulation pulse in the first chamber in response to there being stability in the first chamber, conduction stability, a determined 1:1 association ratio, acceleration of rate, and disassociation of conduction at the onset of acceleration.

79. The apparatus of claim 78 wherein the association ratio determining means further comprises means for determining a 1:1 association ratio in response to the quotient of the second peak divided by the second total being greater than a preset fraction.

80. The apparatus of claim 78 wherein the association ratio determining means further comprises means for determining a 1:1 association ratio in response to the quotient of the first total divided by the second total being in a range of from 0.66 to 1.33.

81. The apparatus of claims 58, 59, or 62, further comprising:

means for applying an antitachycardia pacing therapy to the first chamber in response to a tachyarrhythmia that is determined terminable by a stimulation pulse.

* * * * *